US008752555B2

(12) United States Patent
Goldsby

(10) Patent No.: US 8,752,555 B2
(45) Date of Patent: Jun. 17, 2014

(54) MOUTH GUARD

(75) Inventor: Ricky M. Goldsby, Sherwood, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 77 days.

(21) Appl. No.: 12/928,315

(22) Filed: Dec. 8, 2010

(65) Prior Publication Data

US 2011/0132380 A1 Jun. 9, 2011

Related U.S. Application Data

(60) Provisional application No. 61/283,792, filed on Dec. 9, 2009.

(51) Int. Cl.
*A61C 5/14* (2006.01)

(52) U.S. Cl.
USPC .......................... 128/861; 128/859; 128/857

(58) Field of Classification Search
USPC ............... 128/861, 862, 859, 857, 846, 848, 128/200.26; 433/6, 140; 600/195; 602/902
See application file for complete search history.

(56) References Cited

U.S. PATENT DOCUMENTS

| 2,669,988 | A | * | 2/1954 | Carpenter | 128/861 |
|---|---|---|---|---|---|
| 2,882,893 | A | | 4/1959 | Godfroy | |
| 3,139,088 | A | | 6/1964 | Galleher, Jr. | |
| 3,513,838 | A | | 5/1970 | Foderick | |
| 4,112,936 | A | | 9/1978 | Blachly | |
| 4,425,911 | A | | 1/1984 | Luomanen et al. | |
| 5,235,991 | A | | 8/1993 | Minneman | |
| 5,259,762 | A | * | 11/1993 | Farrell | 433/215 |
| 5,941,247 | A | * | 8/1999 | Keane | 128/848 |
| 2007/0197876 | A1 | | 8/2007 | Lane | |
| 2009/0241969 | A1 | * | 10/2009 | Walker | 128/848 |

OTHER PUBLICATIONS

Monaca, E., Fock, N., Doehn, M., and Wappler, F., The Effectiveness of Preformed Tooth Protectors During Endotracheal Intubation: An Upper Jaw Model, Anesthesia & Analgesia, Nov. 2007, 1326-1332, vol. 105:5.
Denta-Gard Mouth Protectors, www.dentaguard.com (last visited Sep. 14, 2009).
Endochoice Blox Bite Block, www.endochoice.com (last visited Dec. 1, 2010).
The Endoragard, www.endoragard.com (last visited Sep. 14, 2009).
Bitestrong Bite Blocks, www.instrumentguards.com/biteblock.html (last visited Sep. 14, 2009).

* cited by examiner

*Primary Examiner* — Victoria J Hicks
(74) *Attorney, Agent, or Firm* — Richard Blakely Glasgow

(57) ABSTRACT

A mouth guard including a top mouth piece for engaging the top teeth and a bottom mouth piece for engaging the bottom teeth. The mouth guard also includes a central section having one or more ports for receiving an endotracheal tube, oral gastric tube, and/or oral suction tube. In a first preferred embodiment, a top portion of the central section is attached to the top mouth piece, and a bottom portion of the central section is attached to the bottom mouth piece. In a second preferred embodiment, the entire central section is attached to the bottom mouth piece. The top and bottom mouth pieces are capable of interlocking via male engaging members and female recesses.

8 Claims, 8 Drawing Sheets

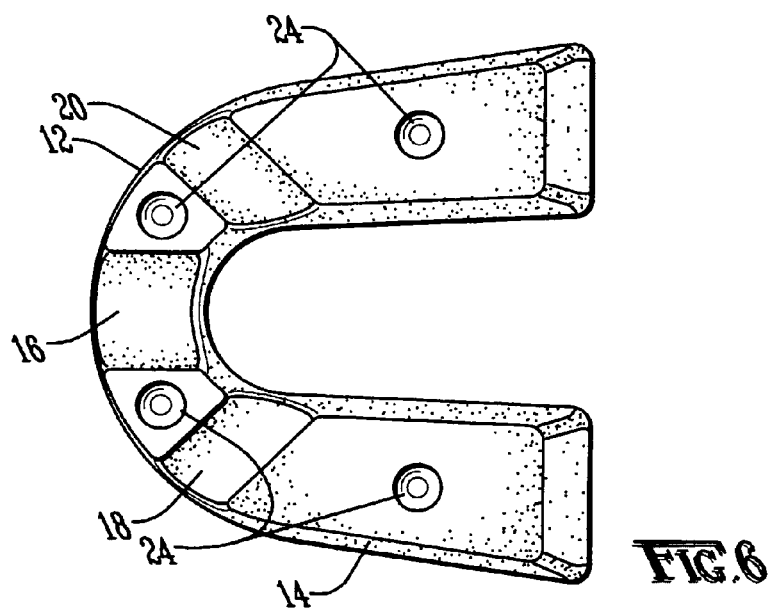
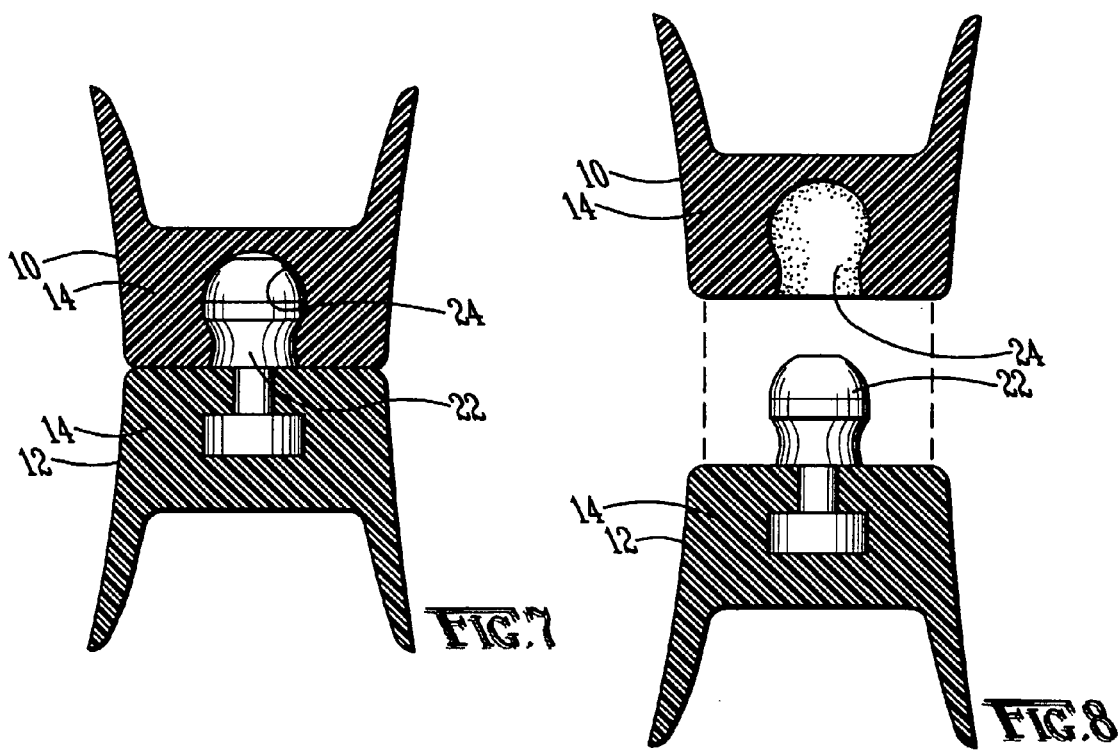

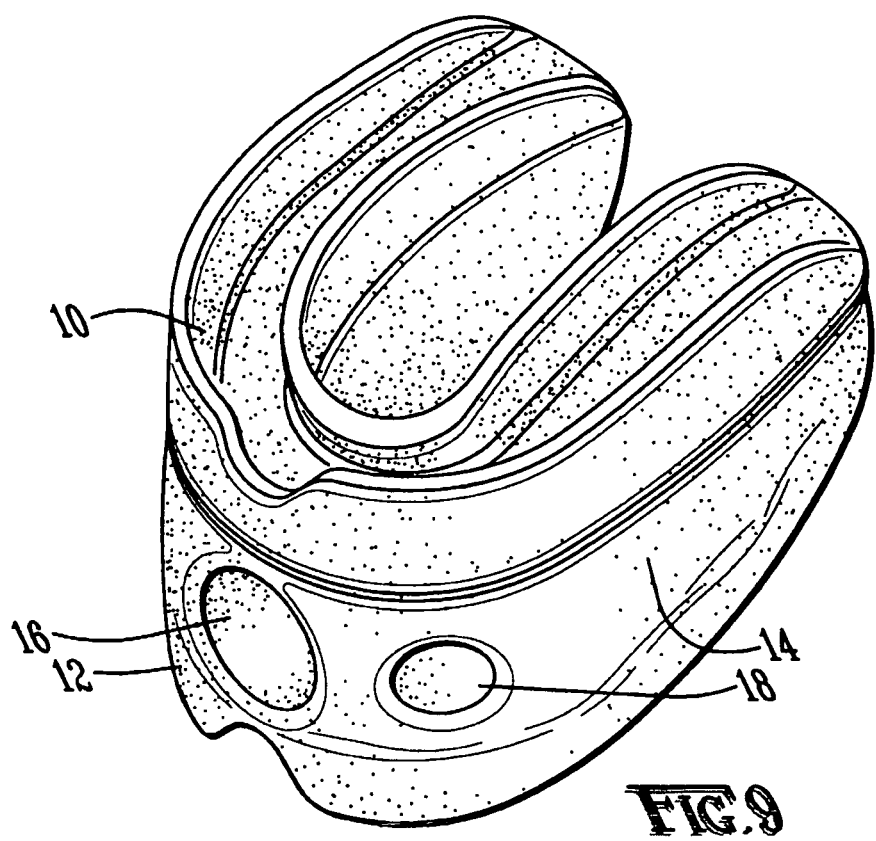

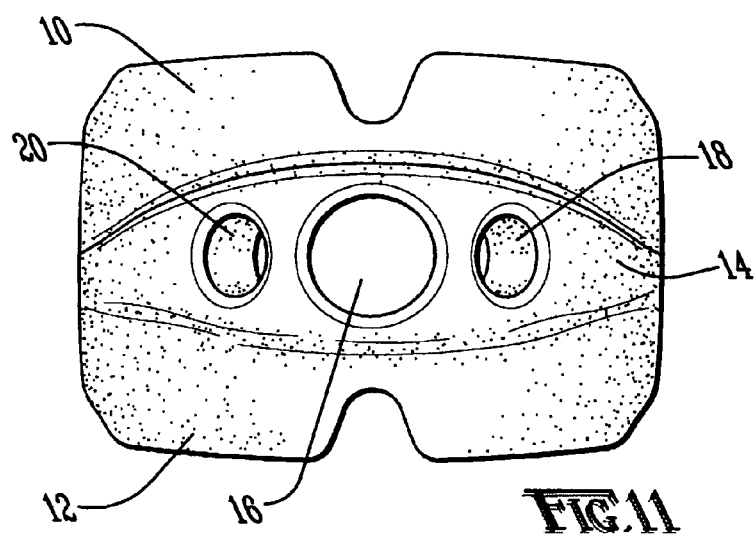
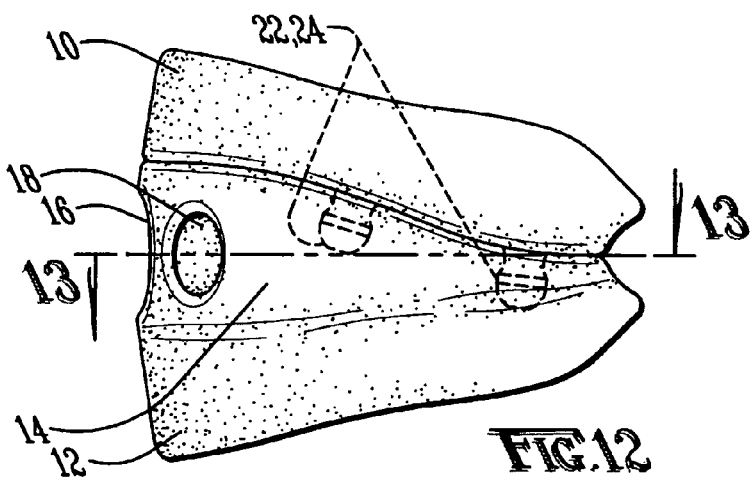

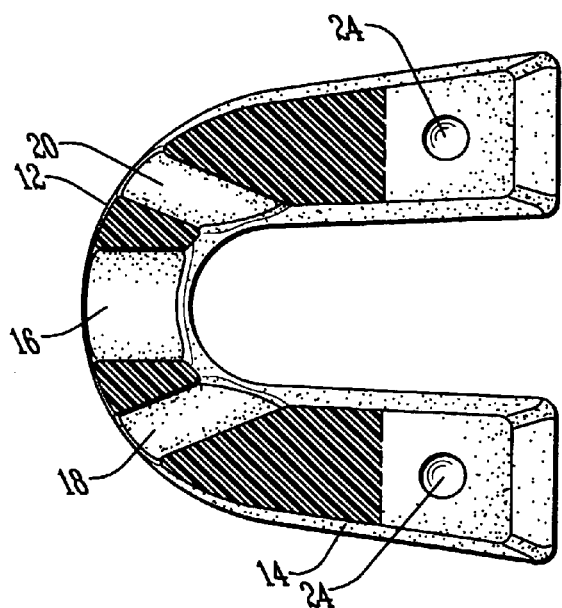
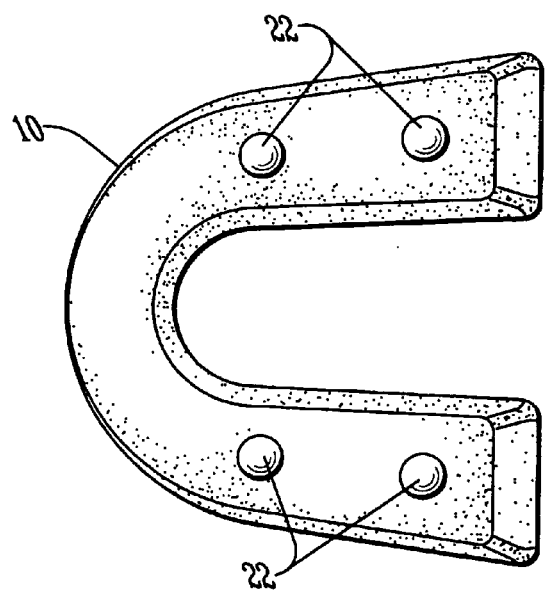

US 8,752,555 B2

MOUTH GUARD

CROSS REFERENCE TO RELATED APPLICATIONS

This application claims the benefit of U.S. Provisional Application No. 61/283,792, entitled "Mouth Guard" and filed on Dec. 9, 2009. The complete disclosure of said provisional patent application is hereby incorporated by reference.

STATEMENT REGARDING FEDERALLY SPONSORED RESEARCH OR DEVELOPMENT

Not applicable

BACKGROUND OF THE INVENTION

1. Field of the Invention

The present invention relates to a mouth guard and more particularly to a mouth guard for post-intubated patients and patients undergoing a bronchoscopy or other like procedures.

2. Brief Description of the Related Art

Mouth guards are necessary during certain medical treatments to protect the patient's teeth and tongue, as well as any medical equipment in the patient's mouth. For example, a mouth guard is essential when treating a patient that is seizing to prevent the patient from damaging their teeth by severe clinching of the teeth in addition to protecting the patient's tongue from potential trauma that could result from biting down on it during the seizure. Alternatively, for a patient having a bronchoscopy or a similar procedure performed, the mouth guard is useful for protecting the bronchoscope or other instrument positioned in the patient's mouth.

The use of mouth guards during medical procedures is well known. U.S. Pat. No. 2,669,988 to Carpenter teaches a teeth protector that rests entirely within the patient's mouth comprising a "U-shaped web or cushion which is adapted to be clamped between the teeth of the upper and lower jaws when the device is in place for use and sufficient length to underlie all the teeth of the upper jaw and to overlie all the teeth of the lower jaw." U.S. Pat. No. 4,112,936 to Blachly teaches a bite block with "an aperture formed centrally through the block between such surfaces and communicating between the interior and exterior of the block for matingly receiving and frictionally holding a tongue depressor type oral airway tube." Likewise, U.S. Pat. No. 4,425,911 to Luomanen teaches a bite block with the body of block "having a central channel open at the top and a pair of open side channels on either side of the central channel."

While the prior art teaches mouth guards allowing for multiple tubes and designed to protect the teeth and tongue of patients as well as the medical equipment in the patient's mouth during intubation, the inventor has found that these mouth guards do not adequately allow medical professionals to adjust the tubes in the patient's mouth to prevent pressure sores that commonly result from long durational contact between the tube and the mouth or throat of the patient. Additionally, the inventor believes that the insertion of full mouth guards is psychologically damaging to the conscious patient because of the bulk of the common mouth guard and the instant strain on the mouth. It would therefore be desirable to develop a mouth guard that is comprised of two interlocking pieces that would result in less psychological impact on the patient during insertion of the mouth guard, and that can easily be unlocked to allow movement of tubes to prevent sores from resulting from the contact of the tubes in the patient's mouth and throat.

BRIEF SUMMARY OF THE INVENTION

The present invention is directed to a mouth guard comprising: (a) a first mouth piece comprising a first surface and a second surface, said first surface adapted to receive the top teeth of a subject; (b) a second mouth piece comprising a first surface and a second surface, said second surface adapted to receive the bottom teeth of a subject; (c) a central section comprising at least one port, wherein a first portion of said central section is attached to said second surface of said first mouth piece and a second portion of said central section is attached to said first surface of said second mouth piece; and (d) means for interlocking said first portion of said central section and said second portion of said central section.

The present invention is also directed to a mouth guard comprising: (a) a first mouth piece comprising a first surface and a second surface, said first surface adapted to receive the top teeth of a subject; (b) a second mouth piece comprising a first surface and a second surface, said second surface adapted to receive the bottom teeth of a subject; (c) a central section comprising at least one port, wherein said central section is attached to said first surface of said second mouth piece; and (d) means for interlocking said first mouth piece and said central section.

The present invention is also directed to methods for using the first preferred embodiment and second preferred embodiment of the mouth guard as described above.

These and other features, objects and advantages of the present invention will become better understood from a consideration of the following detailed description of the preferred embodiments and appended claims in conjunction with the drawings as described following:

BRIEF DESCRIPTION OF THE DRAWINGS

FIG. 6 is a bottom plan view of the top mouth piece of the first preferred embodiment of the present invention.

FIG. 7 is a cross sectional view along the line 7-7 of FIG. 5.

FIG. 8 is an exploded view of FIG. 7.

FIG. 9 is a perspective view of the second preferred embodiment of the present invention.

FIG. 11 is a front elevational view of the second preferred embodiment of the present invention.

FIG. 12 is a left side elevational view of the second preferred embodiment of the present invention.

FIG. 13 is a partial cross sectional view of FIG. 12 along the line 13-13.

FIG. 14 is a bottom plan view of the top mouth piece of the second preferred embodiment of the present invention.

DETAILED DESCRIPTION OF THE INVENTION

Figure 1:
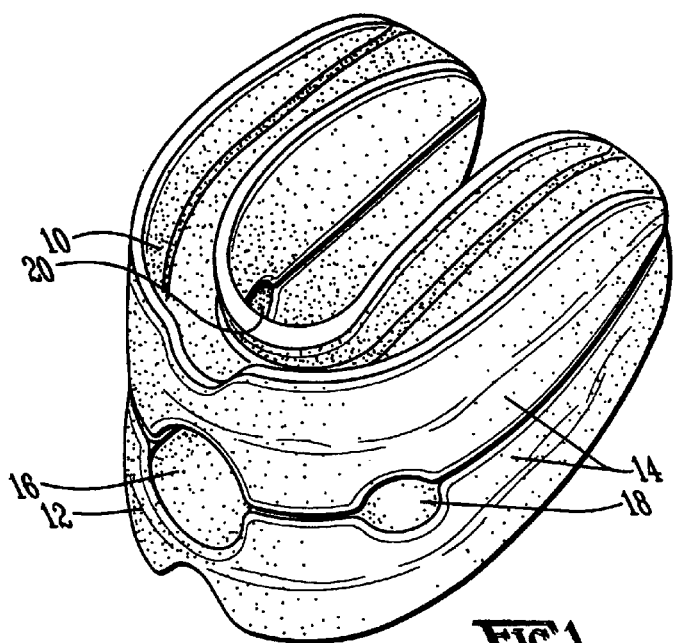
FIG. 1 is a perspective view of the first preferred embodiment of the present invention.
Figure 2:
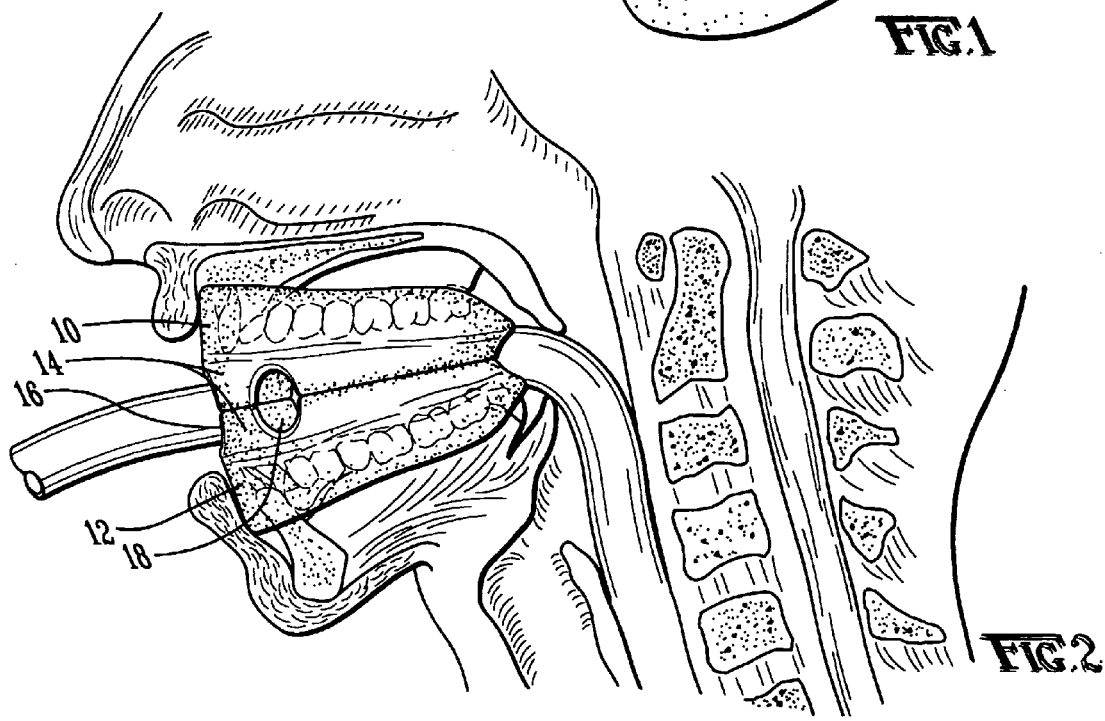
FIG. 2 is a left side elevational view of the first preferred embodiment of the present invention as placed in the patient's mouth with the head of the patient in cross section.
Figure 3:
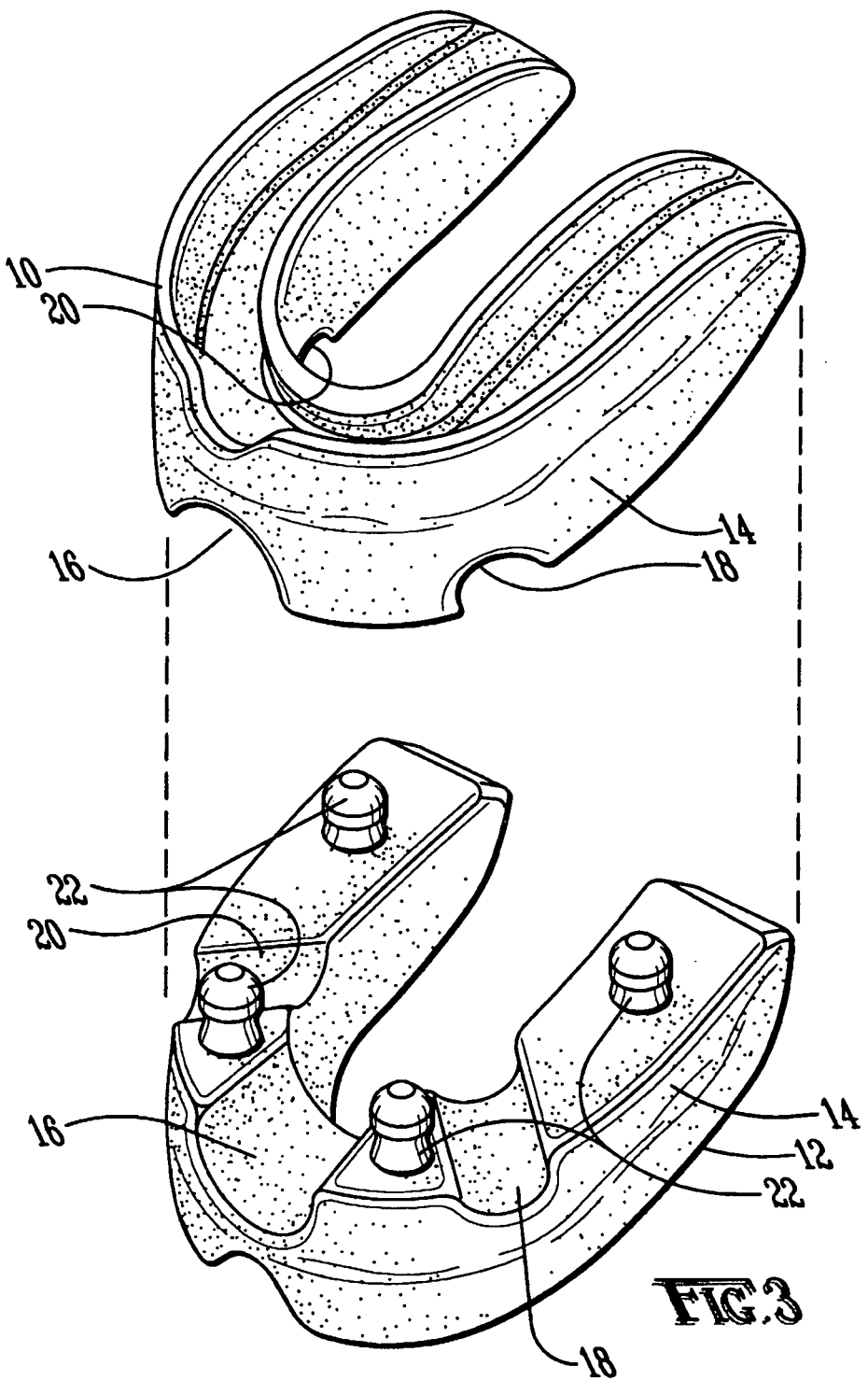
FIG. 3 is an exploded perspective view of the first preferred embodiment of the present invention.
Figure 4:
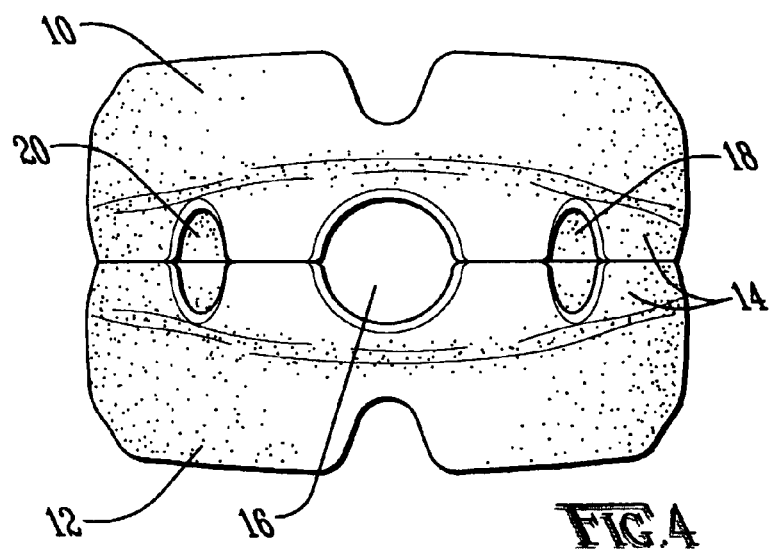
FIG. 4 is a front elevational view of the first preferred embodiment of the present invention.
Figure 5:
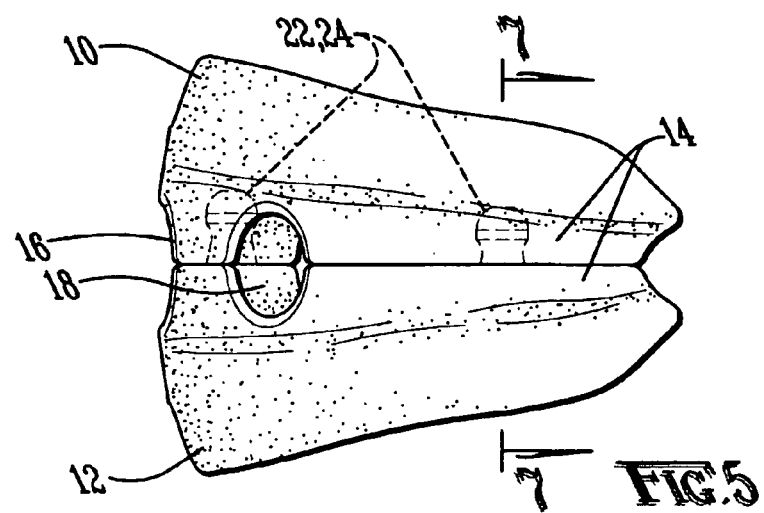
FIG. 5 is a left side elevational view of the first preferred embodiment of the present invention.
Figure 10:
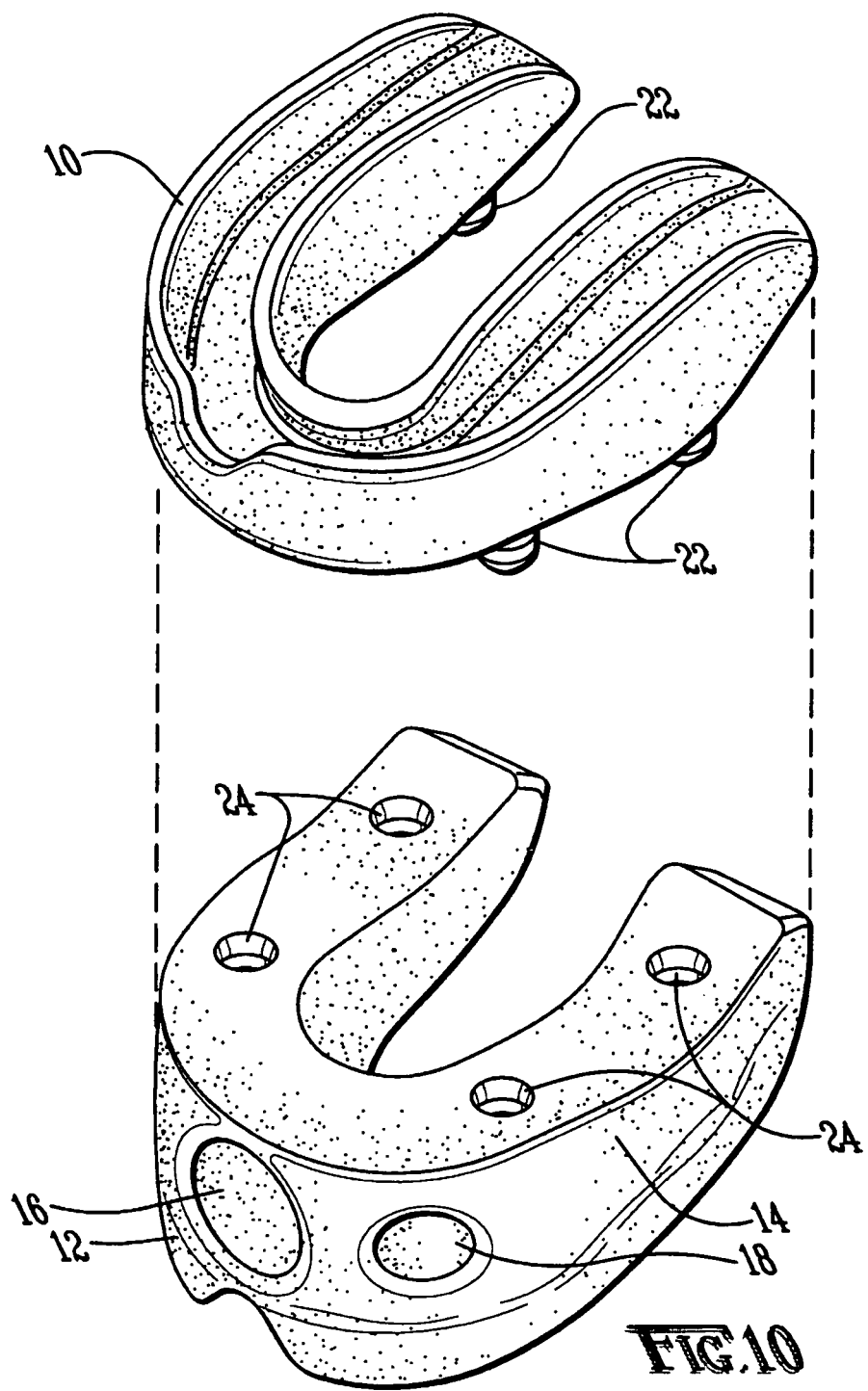
FIG. 10 is an exploded perspective view of the second preferred embodiment of the present invention.

With reference to FIGS. 1-14, the preferred embodiments of the present invention may be described. The mouth guard of the present invention comprises two U-shaped channel mouth pieces to receive the top and bottom teeth of the patient. The top mouth piece 10 and bottom mouth piece 12 are independent of one another and are individually inserted into the patient's mouth. The top mouth piece 10 and bottom mouth piece 12 are attached by the central section 14 of the mouth guard. Both the top and bottom mouth pieces 10, 12 and the connecting central section 14 are composed of a soft dense plastic, such as silicone or other like material. To ensure adequate bite resistance, the central section 14 of the mouth guard has a greater height than the top and bottom mouth pieces 10, 12. While the height of the central section 14 of mouth guard may vary, its height preferably decreases one-half from the front of the guard to the back of the guard for increased comfort to the patient. The central section of the mouth guard contains three ports 16, 18, 20, one directly in the front middle of the guard 16 and the other two on either side of the front port 18, 20. The front port 16 is designed to accommodate an endotracheal tube, thus the size of the port will vary accordingly. The side ports 18, 20 are designed to accommodate an oral gastric tube, oral suction tube or the like, thus the size of the side ports will also vary accordingly. All three ports 16, 18, 20 preferably are made from hard plastic or a similar material that is durable and adapted to receive the aforementioned tubes.

The manner in which the top and bottom pieces are connected can vary. As illustrated in FIGS. 1-8, the first preferred embodiment of the present invention comprises a top mouth piece 10 and bottom mouth piece 12, each piece including the U-shaped channel for receiving the teeth. The top mouth piece 10 has a top portion of the central section 14 fused to it. The bottom mouth piece 12 likewise has a bottom portion of the central section 14 fused to it. The top portion of the central section 14 is preferably the top half of the central section 14, while the bottom portion of the central section 14 is preferably the bottom half of the central section 14. The top and bottom portions of the central section 14 include the corresponding portions of the three ports 16, 18, 20 embedded in the central section 14. Thus, in the preferred embodiment, the top portion of the central section 14 has the top half of the three ports 16, 18, 20 embedded. As such, the bottom portion of the central section 14 has the bottom half of the three ports 16, 18, 20 embedded.

The top mouth piece 10 and bottom mouth piece 12 are interlocked forming one full mouth guard via male engaging members 22 and female recesses 24. Other means for interlocking the top 10 and bottom mouth pieces 12, which would be well-known to those skilled in the art, may alternatively be used. The bottom portion of central section 14, which is attached to the bottom mouth piece 12, preferably has four hourglass-shaped male engaging members 22 on its top surface. The top portion of central section 14, which is attached to the top mouth piece 10, preferably has four complementary hourglass-shaped female recesses 24 on its bottom surface. Alternatively, the male engaging members 22 may be attached to top portion of the central section 14, and the female recesses 24 may be located in the bottom portion of the central section 14. The first set of male engaging members 22 are preferably located between the front port 16 and each side port 18, 20 on the bottom mouth piece 12. Likewise, complementary female recesses 24 are preferably located between the front port 16 and each side port 18, 20 on the top mouth piece 10. The second set of male engaging members 22 are preferably located in the two molar teeth regions of the bottom mouth piece 12. Likewise, complementary female recesses 24 are preferably located in the two molar teeth regions of the top mouth piece 10. The number and location of the male engaging members 22 and female recesses 24 are variable. Once both the top mouth piece 10 and bottom mouth piece 12 are placed in the patient's mouth, the patient's mouth is closed until the four male engaging members 22 fit in the four complementary female recesses 24. Upon insertion into the female recess 24, the male engaging member 22 is compressed as it is forced through the narrow central portion of the hourglass-shaped female recess 24, and subsequently decompressed as it reaches the terminal portion of the female recess 24, which results in the locking of the mouth guard.

After the mouth guard is locked, the top 10 and bottom mouth pieces 12 may be unlocked by manipulation of the male engaging member 22 in the female recess 24. Specifically, the mouth guard can be unlocked by inserting a hard plastic wedge into the seam of the mouth guard and pushing firmly until the top 10 and bottom pieces 12 separate. The plastic wedge should preferably be four inches long, two inches wide, with a graduating height of approximately three inches at the back of the wedge. The separation of the top mouth piece 10 and bottom mouth piece 12 by the plastic wedge causes the compression of the male engaging member 22 as it is forced downward through the narrow central portion of the hourglass-shaped female recess 24 and ultimately results in its complete release from the female recess 24. Because central section 14 is divided through the three ports 16, 18, 20, the mouth guard can be unlocked and the tubes easily moved from one side to the other to prevent contact sores in the patient's mouth and throat. Once the top mouth piece 10 and bottom mouth piece 12 are unlocked, the tube can be slid from one port to another. Closing the patient's mouth will relock the mouth guard.

FIGS. 9-14 illustrate the second preferred embodiment of the present invention. The second preferred embodiment comprises a top mouth piece 10 and bottom mouth piece 12, each including the U-shaped channel for receiving the teeth. Additionally, the bottom mouth piece 12 has the entire central section 14 of the mouth guard fused to it, along with the three full ports 16, 18, 20 embedded in the central section 14. As such, the top mouth piece 10 is comprised solely of the U-shaped channel. Like the first preferred embodiment, the top mouth piece 10 and bottom piece 12 of the second preferred embodiment are interlocked forming a full mouth guard via male engaging members 22 and female recesses 24. Other means for interlocking the top 10 and bottom mouth pieces 12, which would be well-known to those skilled in the art, may alternatively be used. The top mouth piece 10 has four hourglass-shaped male engaging members 22 on its bottom surface. The top surface of the central section 14, which is attached to the bottom mouth piece 12, preferably has four complementary hourglass-shaped female recesses 24. The first set of male engaging members 22 are preferably located in the bicuspid teeth regions of the top mouth piece 10. Likewise, complementary female recesses 24 are preferably located in the bicuspid teeth regions of the bottom mouth piece 12. The second set of male engaging members 22 are preferably located in the molar teeth regions of the top mouth piece 10. Likewise, complementary female recesses 24 are preferably located in the molar teeth regions of the bottom mouth piece 12. The number and location of the male engaging members 22 and female recesses 24 are variable. Once both the top mouth piece 10 and bottom mouth piece 12 are placed in the patient's mouth, the patient's mouth is closed until the four male engaging members 22 fit into the four complementary female recesses 24. Upon insertion into the female recess 24, the male engaging member 22 is compressed as it is forced through the narrow central portion of the hourglass-shaped female recess 24, and subsequently decompressed as it reaches the terminal portion of the female recess 24, which results in the locking of the mouth guard.

After the mouth guard is locked, the top mouth piece 10 and bottom mouth piece 12 may be unlocked by manipulation of the male engaging member 22 in the female recess 24. Specifically, the mouth guard can be unlocked by inserting a hard plastic wedge into the seam of the mouth guard and pushing firmly until the top mouth piece 10 and bottom piece 12 separate. The separation of the top mouth piece 10 and bottom mouth piece 12 by the plastic wedge causes the compression of the male engaging member 22 as it is forced upward through the narrow central portion of the hourglass-shaped female recess 24 and ultimately results in its release from the female recess 24. To reposition the tubes in this embodiment of the present invention, the bottom piece 12 of the mouth guard must be removed from the patient's mouth completely for the tube to be moved to a different port and reinserted into the patient's mouth.

Both embodiments of the present invention may be removed from the patient's mouth while in the locked position. To remove the mouth guard, a Yankauer suction wand, which is readily available in medical facilities, is inserted into one of the ports of the mouth guard and with a firm side-to-side rocking motion the mouth guard will be disengaged from the teeth and can be slid out of the patient's mouth. Although the preferred embodiments are described with reference to a manner of interlocking the top mouth piece 10 and bottom mouth piece 12 by means of four hourglass-shaped male engaging members 22 and four complementary hourglass-shaped female recesses 24, the present invention is not so limited and may be practiced with other interlocking mechanisms which would be well known to those of ordinary skill in the art.

The present invention has been described with certain preferred and alternative embodiments that are intended to be exemplary only and not limiting to the full scope of the invention.

What is claimed is:

1. A mouth guard, wherein said mouth guard has a locked position and an unlocked position, said mouth guard comprising:
   (a) a first mouth piece comprising a first surface and a second surface, said first surface of said first mouth piece adapted to receive top teeth of a subject;
   (b) a second mouth piece comprising a first surface and a second surface, said second surface of said second mouth piece adapted to receive bottom teeth of the subject;
   (c) a central section comprising a first port and a second port, wherein a first portion of said central section is attached to said second surface of said first mouth piece, and a second portion of said central section is attached to said first surface of said second mouth piece;
   (d) means for interlocking said first portion of said central section and said second portion of said central section; and
   (e) a cylindrical tube, wherein said cylindrical tube is positioned in said first port, wherein said cylindrical tube is moveable between said first port and said second port when said mouth guard is in said unlocked position, wherein said first port comprises a curved upper surface that is concave with respect to said first portion of said central section and a curved lower surface that is concave with respect to said second portion of said central section, wherein said curved upper and lower surfaces of said first port correspond to the perimeter of said cylindrical tube, wherein said second port comprises a curved upper surface that is concave with respect to said first portion of said central section and a curved lower surface that is concave with respect to said second portion of said central section, wherein said curved upper and lower surfaces of said second port correspond to the perimeter of said cylindrical tube.

2. The mouth guard of claim 1 wherein said first mouth piece, said second mouth piece, and said central section are made from a soft dense plastic.

3. The mouth guard of claim 2 wherein said soft dense plastic is silicone.

4. The mouth guard of claim 1 wherein said first portion of said central section comprises at least one female recess and said second portion of said central section comprises at least one male engaging member, said at least one female recess adapted to receive said at least one male engaging member.

5. The mouth guard of claim 1 wherein a height of said central section is greater than a height of said first mouth piece and said second mouth piece.

6. The mouth guard of claim 1 wherein said central section decreases in height from a front of said mouth guard to a back of said mouth guard.

7. The mouth guard of claim 1 wherein said central section comprises a third port.

8. A method comprising:
   (a) opening a mouth of a subject;
   (b) placing a first mouth piece in said mouth of said subject, wherein said first mouth piece engages top teeth of said subject, wherein a first portion of a central section is attached to said first mouth piece and wherein said first portion of said central section comprises a top half of a first port and a top half of a second port;
   (c) placing a second mouth piece in said mouth of said subject, wherein said second mouth piece engages bottom teeth of said subject, wherein a second portion of said central section is attached to said second mouth piece and wherein said second portion of said central section comprises a bottom half of said first port and a bottom half of said second port;
   (d) closing said subject's mouth, thereby interlocking said first mouth piece and said second mouth piece, wherein a tube is positioned within said first port; and
   (e) unlocking said first mouth piece and said second mouth piece, and moving said tube from said first port to said second port to prevent contact sores in said mouth of said subject.

* * * * *